(12) United States Patent
Childress

(10) Patent No.: US 12,318,494 B2
(45) Date of Patent: Jun. 3, 2025

(54) METHODS AND SYSTEMS FOR UV-BASED AIRCRAFT DECONTAMINATION

(71) Applicant: The Boeing Company, Chicago, IL (US)

(72) Inventor: Jamie J. Childress, Mercer Island, WA (US)

(73) Assignee: THE BOEING COMPANY, Arlington, VA (US)

( * ) Notice: Subject to any disclaimer, the term of this patent is extended or adjusted under 35 U.S.C. 154(b) by 800 days.

(21) Appl. No.: 17/343,425

(22) Filed: Jun. 9, 2021

(65) Prior Publication Data

US 2021/0402023 A1 Dec. 30, 2021

Related U.S. Application Data

(60) Provisional application No. 63/044,624, filed on Jun. 26, 2020.

(51) Int. Cl.
*A61L 2/10* (2006.01)
*A61L 2/26* (2006.01)
*B64D 11/00* (2006.01)

(52) U.S. Cl.
CPC ........ *A61L 2/10* (2013.01); *A61L 2/26* (2013.01); *B64D 11/00* (2013.01); *A61L 2202/11* (2013.01)

(58) Field of Classification Search
CPC ..... A61L 2/10; A61L 2/24; A61L 2/26; A61L 2202/11; B64D 11/00
See application file for complete search history.

(56) References Cited

U.S. PATENT DOCUMENTS

2011/0291995 A1 12/2011 Shr et al.
2017/0081874 A1 3/2017 Daniels
(Continued)

FOREIGN PATENT DOCUMENTS

CN 108915361 A 11/2018
EP 3913169 A4 11/2021
(Continued)

OTHER PUBLICATIONS

Corning(R) HPFS(R) 7979, 7980, 8655 Fused Silica: Optical Materials Product Information. 2015. (Year: 2015).*
(Continued)

*Primary Examiner* — Timothy C Cleveland
(74) *Attorney, Agent, or Firm* — MH2 Technology Law Group LLP

(57) ABSTRACT

Described herein are methods and systems for decontaminating surfaces on aircraft from pathogens using UV lights with wavelengths between about 200 nanometers and about 240 nanometers. These wavelengths are able to effectively decontaminate pathogens while remaining safe to humans. In other words, humans can remain in decontamination zones during operation of these systems. Furthermore, UV transparent apparatuses, such as door handles, allow decontamination of all surfaces of these apparatuses whether these surfaces are directly or indirectly exposed to the UV light. The indirect exposure is provided by the UV lights passing through the apparatus. Therefore, even surfaces without a line of sight to UV light sources are decontaminated. As such, these methods and systems allow to achieve effective decontamination of an apparatus with a complex surface (e.g., a door handle) without requiring many UV light sources positioned around this apparatus.

20 Claims, 8 Drawing Sheets

(56) References Cited

U.S. PATENT DOCUMENTS

2017/0333580 A1 11/2017 Cahan et al.
2018/0154029 A1* 6/2018 Shr ........................... A61L 2/10
2021/0361795 A1* 11/2021 Carini ................... E05B 1/0069

FOREIGN PATENT DOCUMENTS

JP      2011-245305 A    12/2011
WO   2019/237001 A1   12/2019

OTHER PUBLICATIONS

Childress, Jamie J., Sanitizing System, U.S. Appl. No. 63/042,898, filed Jun. 23, 2020.
Childress, Jamie J., Sanitizing System, U.S. Appl. No. 63/042,904, filed Jun. 23, 2020.
Communication From the Examining Division of the European Patent Office, Application No. 21181687.1, Dated Feb. 22, 2023.
European Application Serial No. 21181687.1, Search Report dated Feb. 4, 2022, 8 pgs.
Miyabe, Aiko (JP Examiner), Notice of Reasons for Refusal issued Mar. 12, 2025 in corresponding Japanese Application No. 2021-106399 (in English and Japanese), 10 pages.

\* cited by examiner

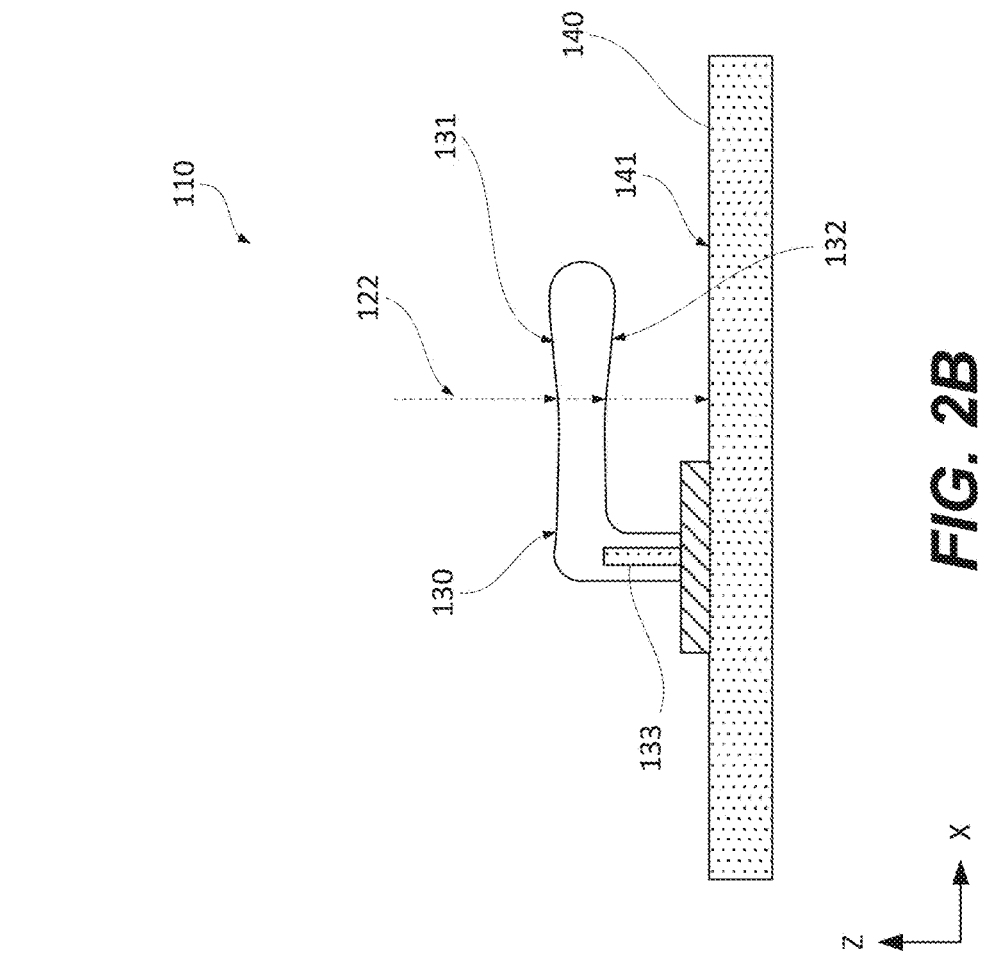
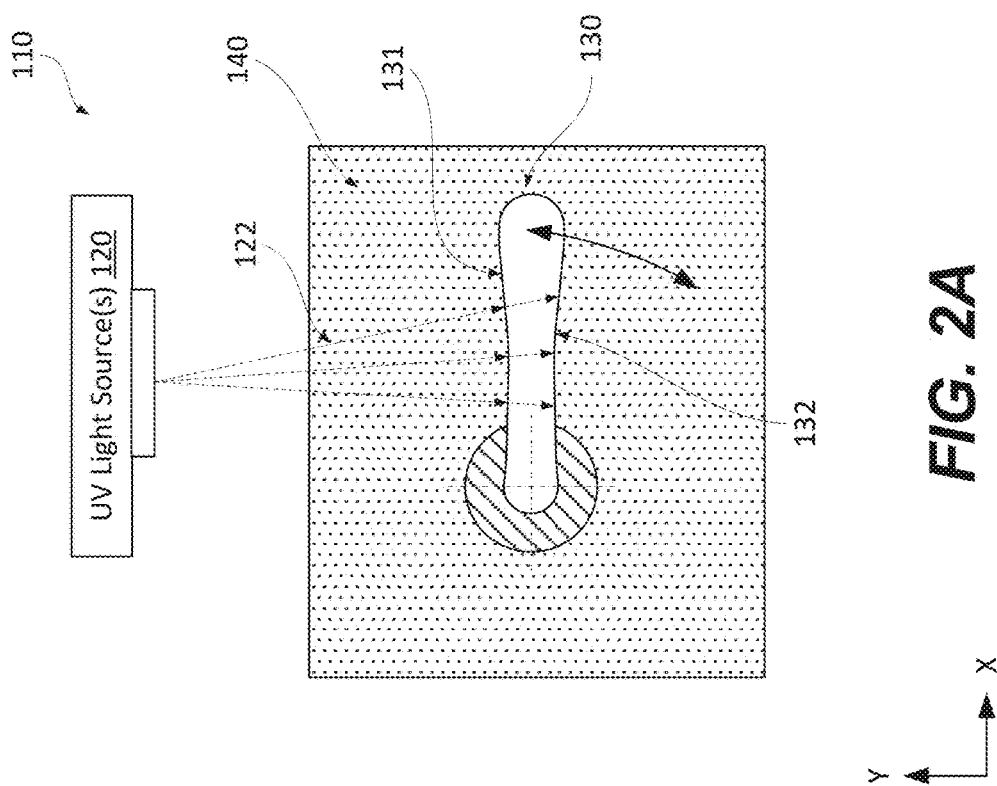

METHODS AND SYSTEMS FOR UV-BASED AIRCRAFT DECONTAMINATION

CROSS-REFERENCE TO RELATED APPLICATIONS

This application claims the benefit under 35 U.S.C. § 119(e) of U.S. Provisional Patent Application 63/044,624, filed on Jun. 6, 2021, which is incorporated herein by reference in its entirety for all purposes.

BACKGROUND

Commercial aircraft include an interior cabin with various facilities, such as lavatories and galley kitchens. During a typical flight, various surfaces in these facilities may become contaminated. For example, passengers and flight attendants contact door handles to access lavatories and may sneeze in proximity to these handles. In short, a door handle and other like components may be covered with various contaminants, such as viruses, bacteria, and other pathogens or microbial contaminants.

A conventional approach involves flight attendants periodically cleaning such surfaces. Furthermore, ground-based cleaning personnel conducts comprehensive decontamination between flights. However, cleaning each touch surface between two consecutive uses can be difficult if possible at all. As such, various contaminants may remain on particular surfaces which may pose real and/or perceived health concerns to future passengers.

SUMMARY

Described herein are methods and systems for decontaminating surfaces on aircraft from pathogens using UV lights with wavelengths between about 200 nanometers and about 240 nanometers. These wavelengths can effectively decontaminate pathogens while being safe for humans. In other words, humans can remain in decontamination zones during the actual operation of these systems. Furthermore, UV transparent apparatuses, such as door, cabinet, and other handles, allow decontamination of all surfaces of these apparatuses whether these surfaces are directly or indirectly exposed to UV light. The indirect exposure is provided by the UV lights passing through the transparent apparatus. Therefore, even surfaces without a direct line of sight to UV light sources are decontaminated. As such, these methods and systems allow achieving effective decontamination of an apparatus with a complex surface (e.g., a door, cabinet, or another handle) without requiring many UV light sources positioned around this apparatus.

BRIEF DESCRIPTION OF THE DRAWINGS

FIG. 2A is a schematic top view of a decontamination system, comprising a UV light source and a UV transparent apparatus, such that the UV light source is configured to decontaminate all surfaces of the UV transparent apparatus, in accordance with some examples.

FIG. 2B is another schematic cross-sectional side view of a decontamination system, comprising a UV light source and a UV transparent apparatus, such that the UV light source is configured to decontaminate all surfaces of the UV transparent apparatus as well as an object surface, shadowed by the UV transparent apparatus, in accordance with some examples.

DETAILED DESCRIPTION

In the following description, numerous specific details are set forth in order to provide a thorough understanding of the presented concepts. In some examples, the presented concepts are practiced without some or all of these specific details. In other instances, well-known process operations have not been described in detail so as to not unnecessarily obscure the described concepts. While some concepts will be described in conjunction with the specific examples, it will be understood that these examples are not intended to be limiting.

Introduction

Figure 1:
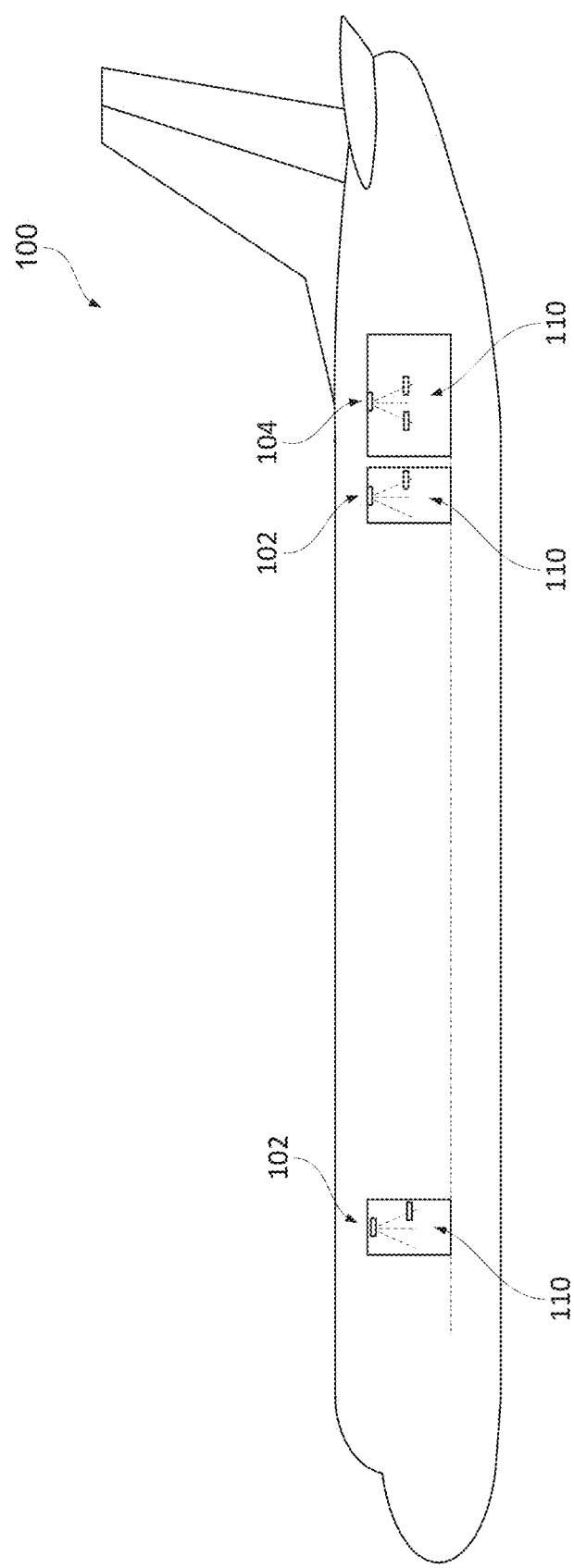
FIG. 1 is a schematic illustration of an aircraft, illustrating decontamination systems positioned in lavatories and galley kitchen of the aircraft, in accordance with some examples.

Decontamination of commercial aircraft can be rather challenging due to various design and operational aspects. FIG. 1 is a schematic illustration of aircraft 100, comprising lavatories 102 and galley kitchen 104, in accordance with some examples. Each of these facilities is used by multiple different people. For example, each lavatory may be used many times during each flight, especially during long intercontinental flights. Furthermore, each of these facilities comprises multiple surfaces, which may be contaminated via direct contact (e.g., touch) or indirect contact (e.g., sneezing, coughing). Some of these surfaces have complex geometries, which makes the decontamination process quite challenging.

While flight attendants may be able to perform some decontamination during the flight, the frequency and thoroughness of this decontamination are limited due to the various complexities, described above. Furthermore, while ground-based cleaning personnel conducts comprehensive decontamination between flights, such decontamination is also needed during the flight.

Methods (described below with reference to FIG. 5) and systems (described below with reference to FIGS. 2A, 2B, 2C, 2D, and 2E) are configured to decontaminate any complex surfaces on aircraft from pathogens using UV lights with wavelengths between about 200 nanometers and about 240 nanometers, such as about 222 nanometers or about 207 nanometers (e.g., within +/−5 nanometers). As noted above, these wavelengths can effectively decontaminate pathogens while remaining safe to humans. In other words, humans can remain in decontamination zones during the operation of these systems.

As further described below and without being restricted to any particular theory, this UV subrange is absorbed by the DNA and RNA of microorganisms, which causes changes in the DNA and RNA structure of these microorganisms. These changes render the microorganisms incapable of replicating, which effectively controls the spread. More specifically, these microorganisms are unable to multiply to infectious numbers within a host, such as a human. It should be noted that conventional approaches focus on the peak of germicidal effectiveness curves. This peak corresponds to about 265-nanometer radiation. Unfortunately, this wavelength is harmful to humans. As such, these conventional decontamination approaches cannot be used while passengers or flight crews are present in areas requiring decontamination. At the same time, it may not be possible or at least practical to isolate specific areas (e.g., lavatories and galley kitchens) from humans while performing the decontamination process. For example, a conventional disinfection cycle lasts about 10-30 minutes, which imposes unreasonable requirements for taking aircraft facilities offline for decontamination. Furthermore, conventional approaches are limited to the "line-of-sight" aspect, only irradiating and decontaminating surfaces within a direct line of sight of a UV light source. Surfaces can be blocked from the light if objects are other objects on the way. Furthermore, non-transparent objects have shadow sides, which can still be contaminated and remain contaminated during these conventional decontamination methods.

Referring again to FIG. 1, aircraft 100 comprises decontamination systems 110 positioned in each of lavatories 102 and galley kitchen 104. Each facility with a risk of pathogen contamination may be designated as a decontamination area and decontamination system 110 is positioned in this area. Decontamination systems 110 rely on a combination of a specific UV subrange (of between about 200 nanometers and about 240 nanometers) and the use of UV transparent apparatuses, such as door handles. The UV transparent apparatuses described herein allow decontamination of all surfaces of these apparatuses whether these surfaces are directly or indirectly exposed to UV light. The indirect exposure is provided by the UV lights passing through the apparatus. For example, a UV transparent apparatus comprises or is formed entirely from quartz glass, such as Corning® HPFS® Fused Silica 7980.

Decontamination System Examples

FIG. 2A is a schematic side view of decontamination system 110 for decontaminating surfaces on aircraft 100 from pathogens, in accordance with some examples. Decontamination system 110 comprises one or more UV light sources 120 and one of more UV transparent apparatuses 130. While FIG. 2A illustrates one UV light source 120 and one UV transparent apparatus 130, one having ordinary skill in the art would understand that decontamination system 110 may comprise any number of UV light sources 120 and any number of UV transparent apparatuses 130. For example, one UV light source 120 may be used for decontaminating multiple UV transparent apparatuses 130, such that all of these UV transparent apparatuses 130 are within a line of sight of this one UV light source 120. Alternatively, multiple UV light source 120 may be used for decontaminating one UV transparent apparatus 130. Finally, multiple UV light source 120 may be used for decontaminating multiple UV transparent apparatuses 130.

Figure 4:
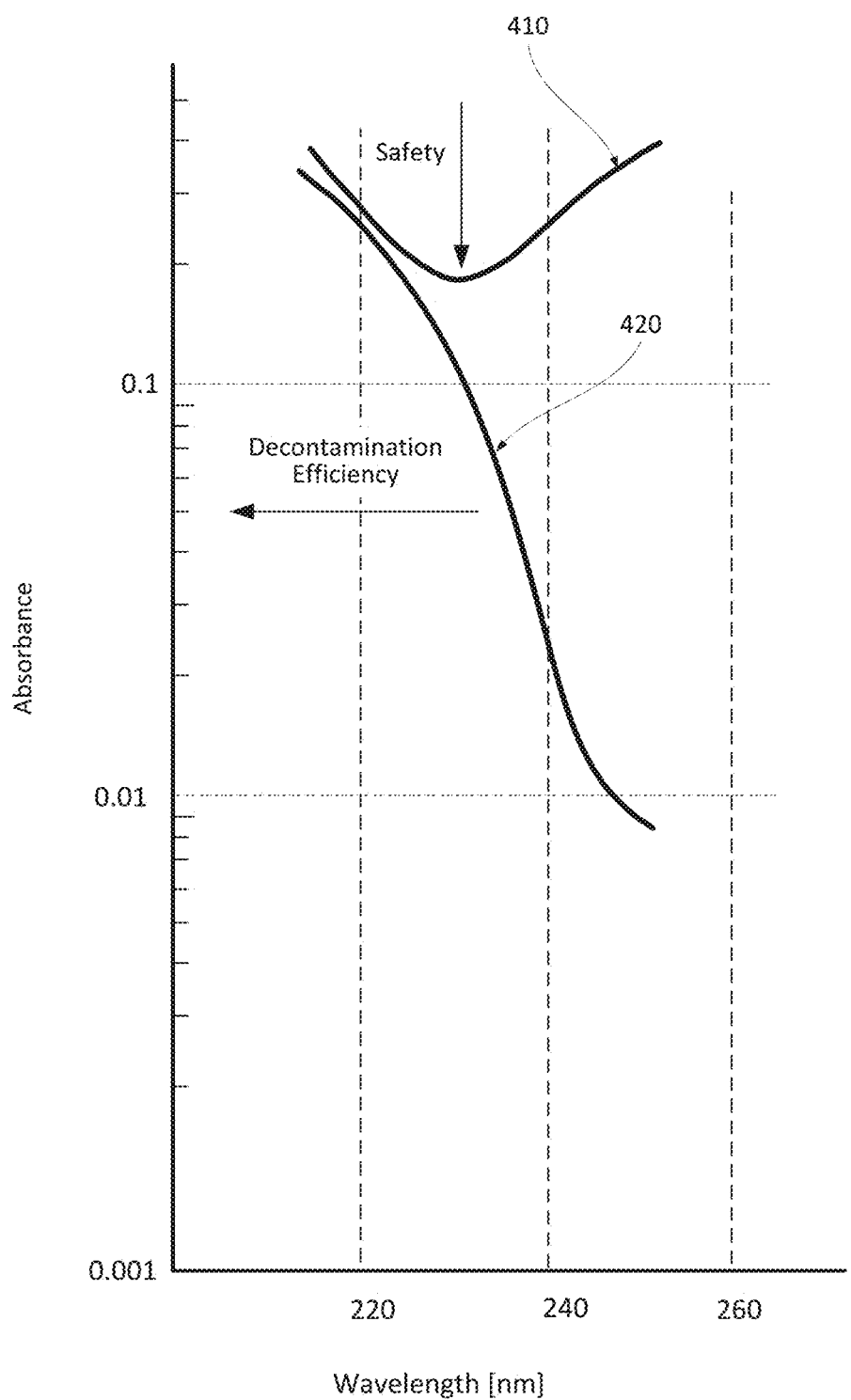
FIG. 4 illustrates absorption plots for DNA and protein as a function of wavelengths in a UV spectrum.

UV light source 120 is configured to generate UV light beam 122 with a wavelength of between about 200 nanometers and about 240 nanometers, or about 200 to about 222 nm, or from about 207 to about 222 nm. It should be noted that wavelengths of 200-240 nanometers represent only a small subrange of a shortwave ultraviolet-C, which is conventionally used for ultraviolet germicidal irradiation. The shortwave ultraviolet-C spans 100-280 nanometers. Without being restricted to any particular theory, it is believed that this 200-240 nanometer subrange is particularly effective with pathogen decontamination while being safe to humans, which will now be described with reference to FIG. 4. Specifically, FIG. 4 illustrates absorption plots for DNA and protein as a function of wavelengths in a UV spectrum. Line 410 corresponds to the DNA absorption and represents the safety of the UV exposure. The lower DNA absorption is desired from the human safety standpoint. Line 420 corresponds to the protein absorption and decontamination efficiency, with the higher protein absorption corresponding to the higher decontamination efficiency. The UV absorption effectively deactivates pathogen by causing various internal changes. The 200-240 nanometer subrange represents a deoxyribonucleic acid (DNA) absorption "well" with sufficiently high protein absorption. While not shown in FIG. 4, the decontamination efficiency for wavelengths lower than 200 nanometers. For example, a 172-nanometer wavelength (produced by a xenon-type light source) has about 10 times lower decontamination efficiency for typical pathogens (e.g., fungus) than a 220-nanometer wavelength.

The human safety aspect of the 200-240 nanometer subrange allows operating UV light source 120 while people are within the line of sight. In other words, decontamination system 110 does not need to monitor the presence of the people within the line of sight of UV light source 120 and selectively turn on and turn off UV light source 120 depending on the presence. In some examples, UV light source 120 operates continuously.

In some examples, UV light source 120 is one of the krypton chloride-type light sources (producing 222-nanometer wavelengths) or krypton bromide-type light sources (producing 207-nanometer wavelengths). Other types of light sources capable of generating wavelengths within the 200-240 nanometer subrange are also within the scope.

Figure 2C:
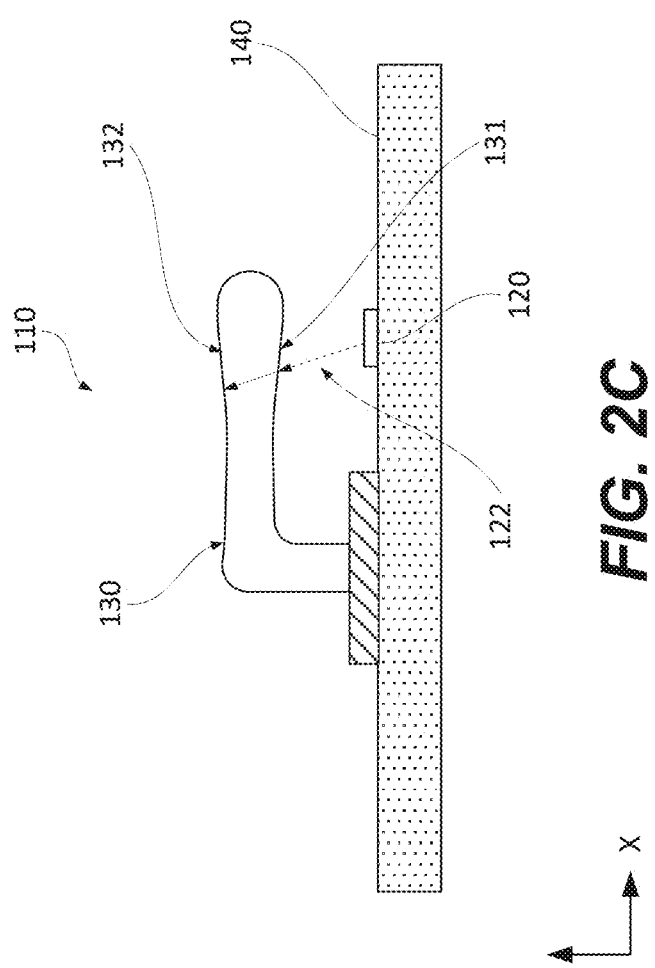
FIG. 2C is yet another schematic side view of a decontamination system, comprising a UV light source and a UV transparent apparatus, such that the UV light source is positioned on an object, which supports the UV transparent apparatus, in accordance with some examples.

Referring to FIGS. 2A, 2B, and 2C, UV transparent apparatus 130 comprises first transparent surface 131 and second transparent surface 132, wherein the second surface is shadowed by the first transparent surface. In some embodiments, the second surface is located behind or under the UV transparent apparatus 130 and, in some examples, the second surface may or may not be transparent. UV transparent apparatus 130 comprises a material, which is transparent to the wavelength of between about 200 nanometers and about 240 nanometers, such as about 200 nanometers to about 222 nm, or from about 207 nanometers to about 220 nm. This material forms first transparent surface 131 and second transparent surface 132. This transparency characteristic of UV transparent apparatus 130 allows UV light beam to pass through UV transparent apparatus 130 and decontaminate both first transparent surface 131 and second transparent surface 132.

For example, first transparent surface 131 is in a direct line of sight of one or more UV light sources 120 such that first transparent surface 131 is directly exposed to one or more UV light beams 122 for decontamination of first transparent surface 131 from the pathogens on first transparent surface 131. This decontamination occurs by the direct exposure of first transparent surface 131.

Second transparent surface 132 is indirectly exposed to one or more UV light beams 122. Second transparent surface 132 is located on the opposite side of the first transparent surface 131 and is not in direct line of sight of the UV light source 120. More specifically, second transparent surface 132 is decontaminated from the pathogens by the transmission of one or more UV light beams 122 through UV transparent apparatus 130 between first transparent surface 131 and second transparent surface 132. More specifically, one or more UV light beams 122 pass through first transparent surface 131, through the body of UV transparent apparatus 130 positioned between first transparent surface 131 and second transparent surface 132, and finally through second transparent surface 132 at which point the pathogens (disposed on second transparent surface 132) are decontaminated.

In some examples, the transmission of one or more UV light beams 122 through UV transparent apparatus 130 between first transparent surface 131 and second transparent surface 132 is at least about 80% or, more specifically, from about 80% to about 99% or from about 90% to about 99% and can even reach up to 100%. Such transparency (in the 200-240 nanometer subrange) requires special materials for UV transparent apparatus 130. For example, UV transparent apparatus 130 comprises or, more specifically, entire formed from quartz glass, such as Corning® HPFS® Fused Silica 7980 or from a material having the UV transmissivity and the ability to be sanitized at from about 207 to about 222 nm. In some examples, first transparent surface 131 and/or second transparent surface 132 is formed from quartz glass or, more specifically, from a transparent material having UV transmissivity and ability to be sanitized at from about 207 to about 222 nm, or even more specifically, from quartz glass, such as Corning® HPFS® Fused Silica 7980.

Figure 2E:
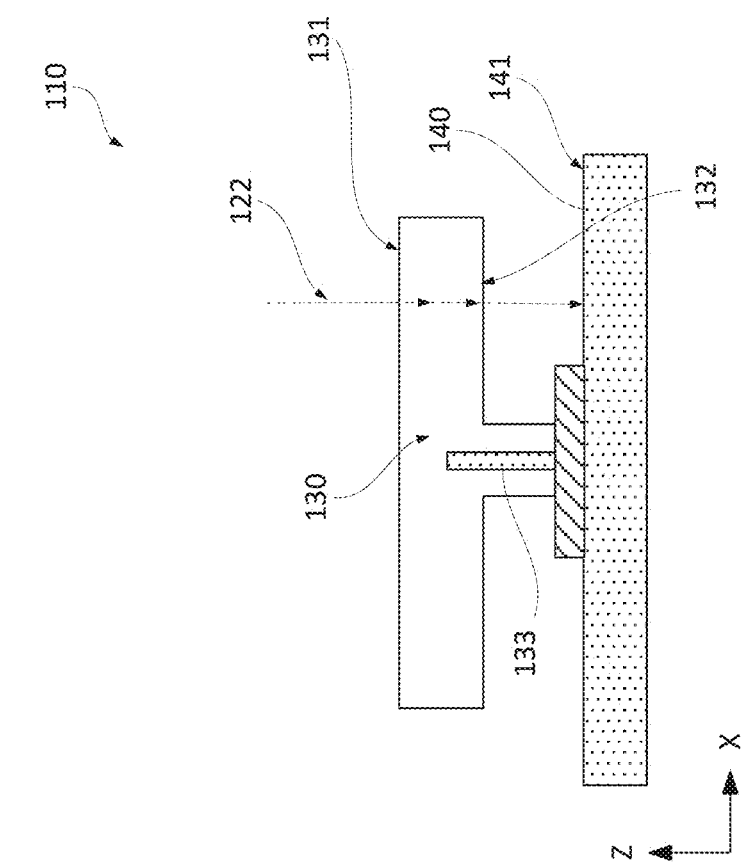
FIGS. 2D and 2E are schematic views of another example of decontamination surfaces, formed by a UV transparent apparatus.
Figure 2D:
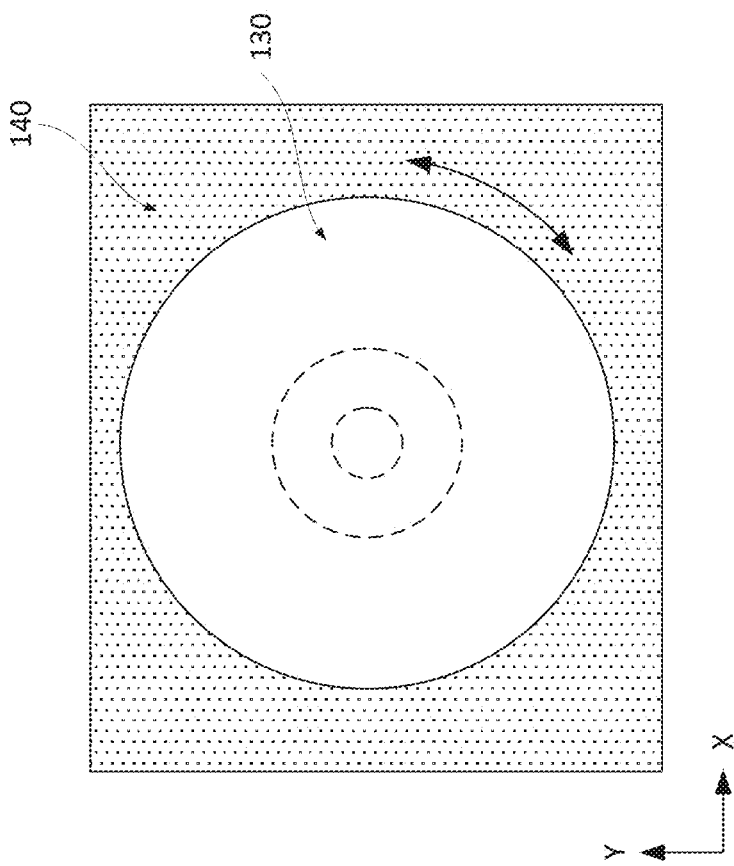

FIGS. 2D and 2E are schematic views of another example of decontamination surfaces, formed by UV transparent apparatus 130.

Figure 3B:
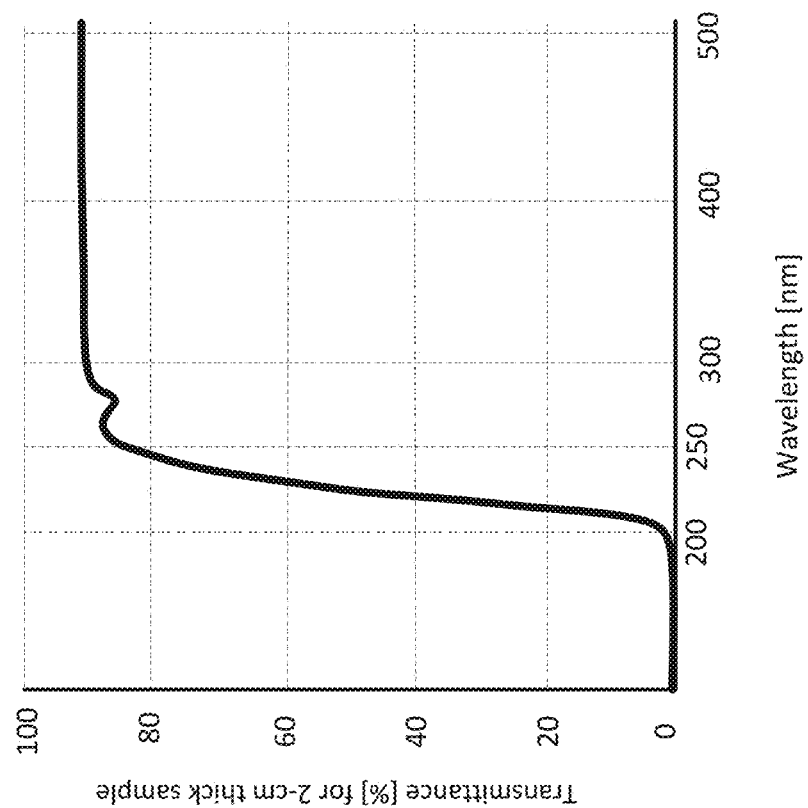
FIG. 3B is a plot showing the lack of UV transmissivity, for wavelengths below 250 nanometers, of conventional borosilicate glass.
Figure 3A:
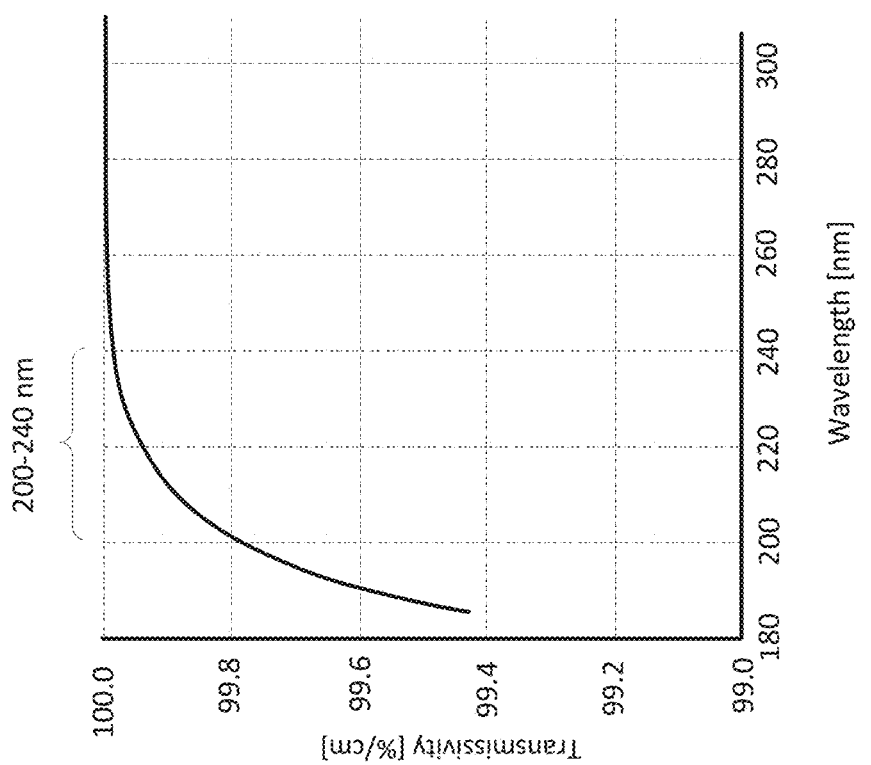
FIG. 3A is a plot showing the UV transmissivity of one material example for a UV transparent apparatus.

FIG. 3A is a plot showing the UV transmissivity of quartz glass, such as Corning® HPFS® Fused Silica 7980. The transmissivity is at least 99% for the entire 200-240 nanometer subrange. As such, the UV exposure of first transparent surface 131 and second transparent surface 132 vary minimally UV transparent apparatus 130 is formed from quartz glass, such as Corning® HPFS® Fused Silica 7980 and when first transparent surface 131 is exposed to UV light sources 120.

FIG. 3B is a plot showing the UV transmissivity of conventional borosilicate glass. More specifically, this plot shows the lack of UV transmissivity, for wavelengths below 250 nanometers, of conventional borosilicate glass.

Referring to FIGS. 2A, 2B, 2C, 2D, and 2E in some examples, UV transparent apparatus 130 is a handle or, more specifically, is a door handle. In general, UV transparent apparatus 130 may be any object with a surface subjected to contamination (e.g., via touching or other means). In a specific example, UV transparent apparatus 130 is a door handle of airplane lavatory 102.

Referring to FIGS. 2A, 2B, 2D, and 2E in some examples, decontamination system 110 further comprises object 140, comprising object surface 141. For example, object 140 may be a door, while UV transparent apparatus 130 is a door handle, pivotably attached to the door. At least a portion of object surface 141 is within a direct light of sight of one or more UV light sources 120. More specifically, UV transparent apparatus 130 is positioned between one or more UV light sources 120 and this portion of object surface 141 and effectively "shadows" the portion of object surface 141. However, due to the transparency of UV transparent apparatus 130 to UV light beams 122, this portion of object surface 141 is indirectly exposed to one or more UV light beams 122. This UV exposure of the portion of object surface 141 provides the decontamination of the portion of object surface 141 from the pathogens. More specifically, one or more UV light beams 122 are transmitted through UV transparent apparatus 130 between first transparent surface 131 and second transparent surface 132 and through a space between second transparent surface 132 and the portion of object surface 141 and deactivate the pathogens on the portion of object surface 141.

Referring to FIG. 2C, in some examples, decontamination system 110 comprises object 140 (e.g., a door) such that UV transparent apparatus 130 (e.g., a door handle) is pivotably attached to object 140 and such that at least one of one or more UV light sources 120 is positioned on object 140. For example, UV light source 120 is positioned on a door.

In some examples, one or more UV light sources 120 comprises multiple UV light sources such that a surface area of first transparent surface 131 is greater than the surface area of second transparent surface 132. It should be noted that first transparent surface 131 is a surface with a direct line of sight to one or more UV light sources 120, while second transparent surface 132 does not have a direct line of sights to one or more UV light sources 120, Decontamination of second transparent surface 132 is performed when UV light beams 122 are transmitted through UV transparent apparatus 130.

Referring to FIG. 2B, in some examples, UV transparent apparatus 130 comprises non- transparent insert 133. For purposes of this disclosure, non-transparent insert 133 is defined as an object not transparent to wavelengths of between about 200 nanometers and about 240 nanometers (e.g., transparency is less than 10% or even less than 1%). In this example, one or more UV light sources 120 are positioned such that non-transparent insert 133 does not shadow any surfaces of UV transparent apparatus 130 from UV light beams 122. Some examples of non-transparent insert 133 include, but are not limited to, portions of a door used for attaching UV transparent apparatus 130 comprising a fastener (e.g., such as a screw, bolt, or the like), to a UV transparent apparatus such as, for example, a door handle. As illustrated in FIG. 2B, the non-transparent insert is located within the material of the UV transparent apparatus 130.

Decontamination Method Examples

Figure 5:
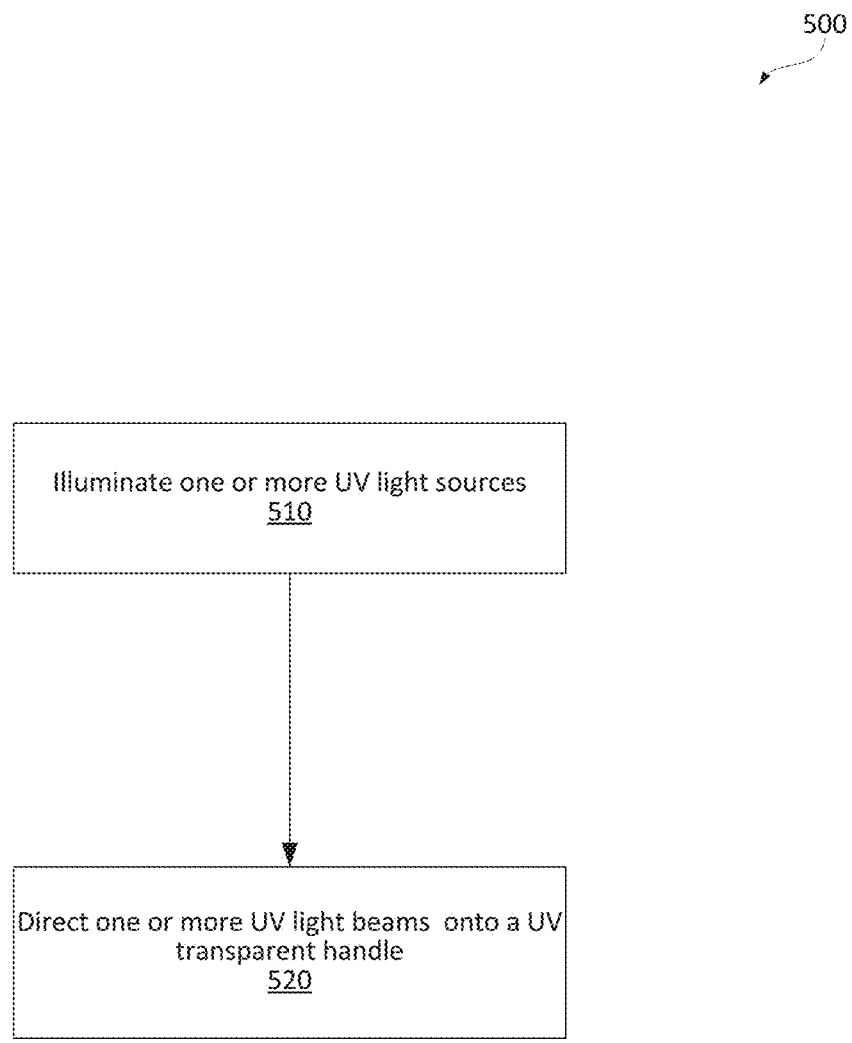
FIG. 5 is a process flowchart corresponding to a method for decontaminating an aircraft from pathogens using a UV light source, in accordance with some examples.

FIG. 5 is a process flowchart corresponding to method 500 for decontaminating aircraft from pathogens using UV light sources 120, in accordance with some examples.

In some examples, method 500 comprises illuminating (block 510) one or more UV light sources 120. This illumination operation generates one or more UV light beams 122 with a wavelength of between about 200 nanometers and about 240 nanometers, such as about 222 nanometers or about 207 nanometers (e.g., within +/−5 nanometers). For example, one or more UV light sources 120 is turned on by a flight attendant or a system controller (e.g., as a part of a general decontamination protocol)

Method 500 proceeds with directing (block 520) one or more UV light beams 122 in a direction of UV transparent apparatus 130. Various examples of UV transparent apparatus 130 are described above with reference to FIGS. 2A, 2B, 2C, 2D, and 2E. In some examples, UV transparent apparatus 130 comprised first transparent surface 131 and second transparent surface 132. First transparent surface 131 is in a direct line of sight of one or more UV light sources 120 such that first transparent surface 131 is directly exposed to one or more UV light beams 122. This direct UV exposure decontaminates first transparent surface 131 from the pathogens. Furthermore, second transparent surface 132 is indirectly exposed to one or more UV light beams 122. One or more UV light beams 122 pass through UV transparent apparatus 130, between first transparent surface 131 and second transparent surface 132, also through each of first transparent surface 131 and second transparent surface 132. This indirect exposure decontaminates second transparent surface 132 from the pathogens by the transmission of one or more UV light beams 122 through UV transparent apparatus 130 between first transparent surface 131 and second transparent surface 132, and In some examples, directing one or more UV light beams 122 onto UV transparent apparatus 130 comprises illuminating at least a portion of object surface 141 of object 140 as, for example, is schematically shown in FIG. 2B. UV transparent apparatus 130 is positioned between this portion of object surface 141 and effective "shadowed" from one or more UV light sources 120 by UV transparent apparatus 130. However, due to the transparency of UV transparent apparatus 130 to wavelengths between about 200 nanometers and about 240 nanometers, this portion of object surface 141 is indirectly exposed by UV light sources 120.

Aircraft Examples

In some examples, methods, and systems described above are used on aircraft and, more generally, by the aerospace industry. Specifically, these methods and systems can be used during the fabrication of aircraft as well as during aircraft service and maintenance.

Figure 6:
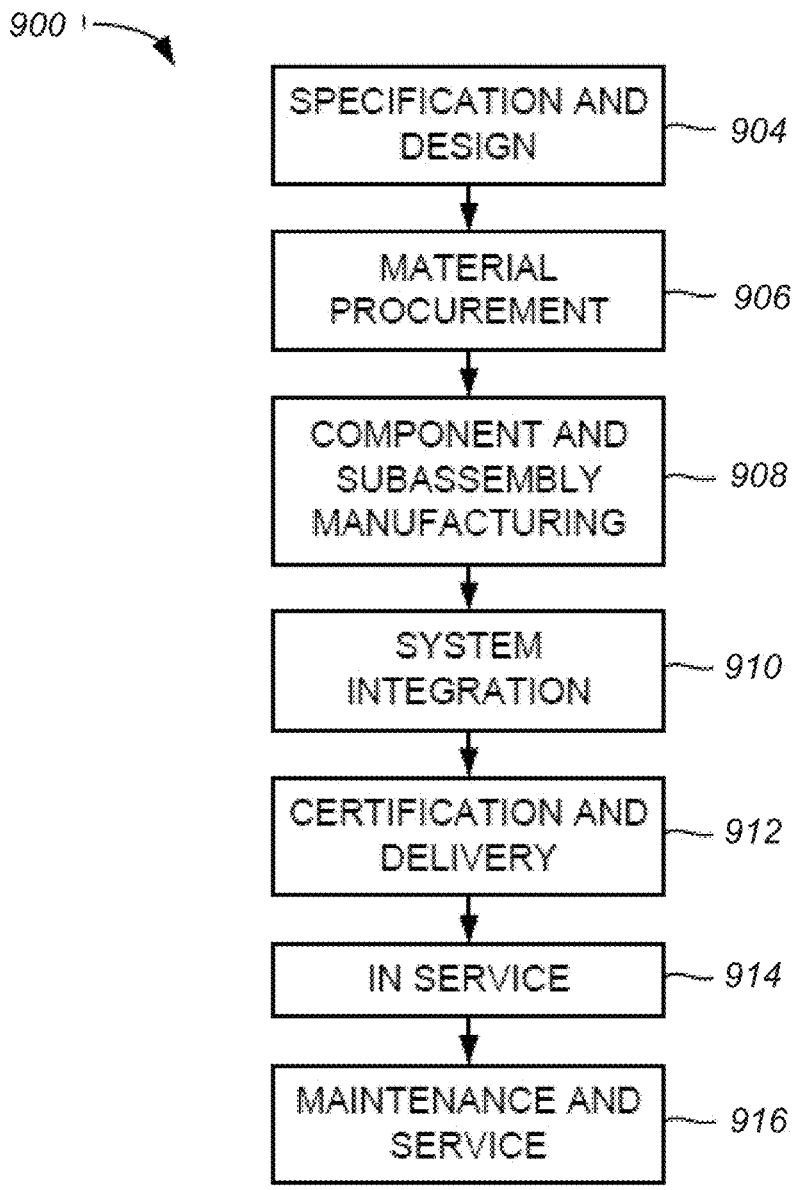
FIG. 6 is a process flowchart corresponding to a method for manufacturing and servicing the aircraft.
Figure 7:
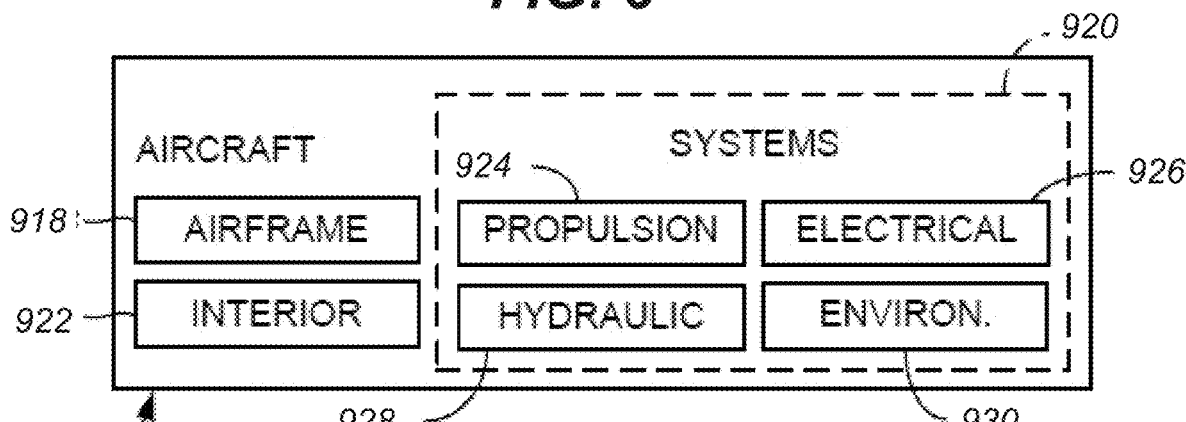
FIG. 7 illustrates a block diagram of an example aircraft, in accordance with some examples.

Accordingly, the apparatus and methods described above are applicable for aircraft manufacturing and service method 900 as shown in FIG. 6 and for aircraft 902 as shown in FIG. 7. During pre-production, method 900 includes specification and design 904 of aircraft 902 and material procurement 906. During production, component, and subassembly manufacturing 908 and system integration 910 of aircraft 902 takes place. Thereafter, aircraft 902 goes through certification and delivery 912 to be placed in service 914. While in service by a customer, aircraft 902 is scheduled for routine maintenance and service 916, which also includes modification, reconfiguration, refurbishment, and so on.

In some examples, each of the processes of method 900 is performed or carried out by a system integrator, a third party, and/or an operator, e.g., a customer. For purposes of this description, a system integrator includes without limitation any number of aircraft manufacturers and major-system subcontractors; a third party includes without limitation any number of vendors, subcontractors, and suppliers; and an operator can be an airline, leasing company, military entity, service organization, and so on.

As shown in HG. 7, aircraft 902 produced by method 900 includes airframe 918 with the plurality of systems 92.0 and interior 922. The airframe 918 includes the wings of the aircraft 902. Examples of systems 920 include one or more propulsion system 924, electrical system 926, hydraulic system 928, and environmental system 930. Any number of other systems can be included.

Apparatus and methods presented herein can be employed during any one or more of the stages of method 900. For example, components or subassemblies corresponding to manufacturing 908 are fabricated or manufactured like components or subassemblies produced while aircraft 902 is in service. Also, one or more apparatus examples, method examples, or a combination thereof are utilized during manufacturing 908 and system integration 910, for example, by substantially expediting assembly of or reducing the cost of an aircraft 902, Similarly, one or more apparatus examples, method examples, or a combination thereof are utilized while aircraft 902 is in service, for example, and without limitation, to maintenance and service 916.

Further Examples

Further, the description includes examples according to the following clauses:

Clause 1. A decontamination system for decontaminating surfaces on an aircraft from pathogens, the decontamination system comprising:

one or more UV light sources, configured to generate one or more UV light beams with a wavelength of between about 200 nanometers and about 240 nanometers; and a UV transparent apparatus, comprising a first transparent surface and a second transparent surface, wherein the UV transparent apparatus comprising a material, transparent to the wavelength of between about 200 nanometers and about 240 nanometers, the material forming the first transparent surface and the second transparent surface, wherein the first transparent surface is in a direct line of sight of the one or more UV light sources such that the first transparent surface is directly exposed to the one or more UV light beams for decontamination of the first transparent surface from the pathogens, wherein the second transparent surface is indirectly exposed to the one or more UV light beams and wherein the second transparent surface is decontaminated from the pathogens by transmission of the one or more UV light beams through the UV transparent apparatus between the first transparent surface and the second transparent surface, and wherein the transmission of the one or more UV light beams through the UV transparent apparatus between the first transparent surface and the second transparent surface is at least about 80%.

Clause 2. The decontamination system of clause 1, wherein the transmission of the one or more UV light beams through the UV transparent apparatus between the first transparent surface and the second transparent surface is at least about 90%.

Clause 3. The decontamination system of any one of clauses 1-2, wherein the first transparent surface is formed from quartz glass.

Clause 4. The decontamination system of any one of clauses 1-3, wherein the first transparent surface is formed from quartz glass, such as Corning® HPFS® Fused Silica 7980.

Clause 5. The decontamination system of any one of clauses 1-4, wherein the UV transparent apparatus is a door handle.

Clause 6. The decontamination system of any one of clauses 1-5, wherein the UV transparent apparatus is a door handle of an airplane lavatory.

Clause 7. The decontamination system of any one of clauses 1-6, further comprising an object, comprising an object surface, wherein at least a portion of the object surface is not within the direct line of sight of the one or more UV light sources such that at least the portion of the object surface is indirectly exposed to the one or more UV light beams, for decontaminating at least the portion of the object surface from the pathogens, by the transmission of the one or more UV light beams through the UV transparent apparatus between the first transparent surface and the second transparent surface and through a space between the second transparent surface and at least the portion of the object surface.

Clause 8. The decontamination system of clause 7, wherein the UV transparent apparatus is pivotably attached to the object.

Clause 9. The decontamination system of any one of clauses 1-8, further comprising an object, wherein:
the UV transparent apparatus is pivotably attached to the object, and
at least one of the one or more UV light sources is positioned on the object.

Clause 10. The decontamination system of any one of clauses 1-9, wherein the one or more UV light sources comprises multiple UV light sources such that a surface area of the first transparent surface is greater than the surface area of the second transparent surface.

Clause 11. A UV transparent apparatus for use on an aircraft, comprising one or more UV light sources, configured to generate one or more UV light beams with a wavelength of between 200 nanometers and 240 nanometers for decontaminating the aircraft from pathogens, the UV transparent apparatus comprising:
a first transparent surface, positioned in a direct line of sight of the one or more UV light sources such that the first transparent surface is directly exposed to the one or more UV light beams for decontamination of the first transparent surface from the pathogens; and
a second transparent surface, indirectly exposed to the one or more UV light beams and wherein the second transparent surface is decontaminated from the pathogens by transmission of the one or more UV light beams through the UV transparent apparatus between the first transparent surface and the second transparent surface,
wherein the transmission of the one or more UV light beams through the UV transparent apparatus between the first transparent surface and the second transparent surface is at least 80%.

Clause 12. The UV transparent apparatus of clause 11, wherein the transmission of the one or more UV light beams through the UV transparent apparatus between the first transparent surface and the second transparent surface is at least 90%.

Cause 13. The UV transparent apparatus of any one of clauses 11-12, wherein the first transparent surface comprises a material having ability to be transparent and sanitized at a UV wavelength of about 222 nm.

Clause 14. The UV transparent apparatus of any one of clauses 11-13, wherein the first transparent surface is formed from quartz glass, such as Corning® HPFS® Fused Silica 7980.

Clause 15. The UV transparent apparatus of any one of clauses 11-14, wherein the UV transparent apparatus is a door handle of a lavatory.

Clause 16. A method for decontaminating surfaces on an aircraft from pathogens, the method comprising:
illuminating one or more UV light sources, thereby generating one or more UV light beams with a wavelength of between about 200 nanometers and about 240 nanometers; and
directing the one or more UV light beams in a direction of a UV transparent apparatus, comprising a first transparent surface and a second transparent surface, wherein:
the first transparent surface is in a direct line of sight of the one or more UV light sources such that the first transparent surface is directly exposed to the one or more UV light beams for decontamination of the first transparent surface from the pathogens,
the second transparent surface is indirectly exposed to the one or more UV light beams and wherein the second transparent surface is decontaminated from the pathogens by transmission of the one or more UV light beams through the UV transparent apparatus between the first transparent surface and the second transparent surface, and
the transmission of the one or more UV light beams through the UV transparent apparatus between the first transparent surface and the second transparent surface is at least 80%.

Clause 17. The method of clause 16, wherein the first transparent surface is formed by a material having ability to be transparent and sanitized at the wavelength of between about 200 nanometers and about 240 nanometers.

Clause 18. The method of any one of clauses 16-17, wherein directing the one or more UV light beams onto the UV transparent apparatus comprises illuminating at least a portion of an object surface of an object shadowed from the one or more UV light sources by the UV transparent apparatus.

Clause 19. The method of clause 18, wherein the object is a door of a lavatory on the aircraft, and wherein the UV transparent apparatus is pivotably coupled to the object.

Clause 20. The method of any one of clauses 1549, wherein the UV transparent apparatus is formed from quartz glass, such as Corning® HPFS® Fused Silica 7980.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatus. Accordingly, the present examples are to be considered illustrative and not restrictive.

What is claimed is:

1. A decontamination system for decontaminating surfaces on an aircraft from pathogens, the decontamination system comprising:
a door;
one or more UV light sources, configured to generate one or more UV light beams with a wavelength of between about 200 nanometers and about 240 nanometers; and
a UV transparent apparatus attached to the door, comprising a first transparent surface and a second transparent surface and a non-transparent insert,
wherein the UV transparent apparatus comprising a material, transparent to the wavelength of between about 200 nanometers and about 240 nanometers, the material forming the first transparent surface and the second transparent surface,
wherein the first transparent surface is in a direct line of sight of the one or more UV light sources such that the first transparent surface is directly exposed to the one or more UV light beams for decontamination of the first transparent surface from the pathogens,
wherein the second transparent surface is indirectly exposed to the one or more UV light beams and wherein the second transparent surface is decontaminated from the pathogens by transmission of the one or more UV light beams through the UV transparent apparatus between the first transparent surface and the second transparent surface, wherein the transmission of the one or more UV light beams through the UV transparent apparatus between the first transparent surface and the second transparent surface is at least about 80% wherein the non-transparent insert comprises a fastener to fasten the UV transparent apparatus to an object, and wherein the non-transparent insert is positioned within the material so as to avoid shadowing the second transparent surface from the one or more UV light beams, and wherein the one or more UV light sources comprise multiple UV light sources such that a surface area of the first transparent surface is greater than a surface area of the second transparent surface.

2. The decontamination system of claim 1, wherein the transmission of the one or more UV light beams through the UV transparent apparatus between the first transparent surface and the second transparent surface is at least about 90%.

3. The decontamination system of claim 1, wherein the first transparent surface is formed from quartz glass.

4. The decontamination system of claim 1, wherein the first second transparent surface is formed from quartz glass.

5. The decontamination system of claim 1, wherein the UV transparent apparatus is a door handle.

6. The decontamination system of claim 1, wherein the UV transparent apparatus is a door handle of an airplane lavatory.

7. The decontamination system of claim 1, wherein the door comprises an object surface, wherein at least a portion of the object surface is not within the direct line of sight of the one or more UV light sources such that at least the portion of the object surface is indirectly exposed to the one or more UV light beams, for decontaminating at least the portion of the object surface from the pathogens, by transmission of the one or more UV light beams through the UV transparent apparatus between the first transparent surface and the second transparent surface and through a space between the second transparent surface and at least the portion of the object surface.

8. The decontamination system of claim 7, wherein the UV transparent apparatus is pivotably attached to the door.

9. The decontamination system of claim 1, wherein: the UV transparent apparatus is pivotably attached to the door, and at least one of the one or more UV light sources is positioned on the door.

10. A UV transparent apparatus for use on an aircraft, comprising:

one or more UV light sources, configured to generate one or more UV light beams with a wavelength of between 200 nanometers and 240 nanometers for decontaminating the aircraft from pathogens;

a first transparent surface, positioned in a direct line of sight of the one or more UV light sources such that the first transparent surface is directly exposed to the one or more UV light beams for decontamination of the first transparent surface from the pathogens;

a second transparent surface, indirectly exposed to the one or more UV light beams and wherein the second transparent surface is decontaminated from the pathogens by transmission of the one or more UV light beams through the UV transparent apparatus between the first transparent surface and the second transparent surface, and a non-transparent insert comprising a fastener to fasten the UV transparent apparatus to an object, wherein the non-transparent insert is positioned within the UV transparent apparatus so as to avoid shadowing the second transparent surface from the one or more UV light beams, wherein the transmission of the one or more UV light beams through the UV transparent apparatus between the first transparent surface and the second transparent surface is at least 80%, and wherein the one or more UV light sources comprise multiple UV light sources such that a surface area of the first transparent surface is greater than a surface area of the second transparent surface.

11. The UV transparent apparatus of claim 10, wherein the transmission of the one or more UV light beams through the UV transparent apparatus between the first transparent surface and the second transparent surface is at least 90%.

12. The UV transparent apparatus of claim 10, wherein the first transparent surface comprises a material having ability to be transparent and sanitized at a UV wavelength of about 222 nm.

13. The UV transparent apparatus of claim 10, wherein the first transparent surface is formed from quartz glass.

14. The UV transparent apparatus of claim 10, wherein the UV transparent apparatus is a door handle of a lavatory.

15. A method for decontaminating surfaces on an aircraft from pathogens, the method comprising:

illuminating one or more UV light sources, thereby generating one or more UV light beams with a wavelength of between about 200 nanometers and about 240 nanometers; and directing the one or more UV light beams in a direction of a UV transparent apparatus, comprising a first transparent surface and a second transparent surface and a non-transparent insert, wherein:

the first transparent surface is in a direct line of sight of the one or more UV light sources such that the first transparent surface is directly exposed to the one or more UV light beams for decontamination of the first transparent surface from the pathogens, the second transparent surface is indirectly exposed to the one or more UV light beams and wherein the second transparent surface is decontaminated from the pathogens by transmission of the one or more UV light beams through the UV transparent apparatus between the first transparent surface and the second transparent surface, the non-transparent insert comprises a fastener to fasten the UV transparent apparatus to an object, and wherein the non-transparent insert is positioned within the material so as to avoid shadowing the second transparent surface from the one or more UV light beams, the transmission of the one or more UV light beams through the UV transparent apparatus between the first transparent surface and the second transparent surface is at least 80%, and the one or more UV light sources comprises multiple UV light sources such that a surface area of the first transparent surface is greater than a surface area of the second transparent surface.

16. The method of claim 15, wherein the first transparent surface is formed by a material having ability to be transparent and sanitized at the wavelength of between about 200 nanometers and about 240 nanometers.

17. The method of claim 15, wherein directing the one or more UV light beams onto the UV transparent apparatus comprises illuminating at least a portion of an object surface of an object shadowed from the one or more UV light sources by the UV transparent apparatus.

18. The method of claim 17, wherein the object is a door of a lavatory on the aircraft, and wherein the UV transparent apparatus is pivotably coupled to the object.

19. The method of claim 15, wherein the first UV transparent surface is formed from quartz glass.

20. The method of claim 15, wherein the second UV transparent surface is formed from quartz glass.

* * * * *

UNITED STATES PATENT AND TRADEMARK OFFICE
CERTIFICATE OF CORRECTION

| | | |
|---|---|---|
| PATENT NO. | : 12,318,494 B2 | Page 1 of 1 |
| APPLICATION NO. | : 17/343425 | |
| DATED | : June 3, 2025 | |
| INVENTOR(S) | : Jamie J. Childress | |

It is certified that error appears in the above-identified patent and that said Letters Patent is hereby corrected as shown below:

On the Title Page

In the Abstract, item (57) Line 16: "(e,g.," should be -- (e.g., --,

In the Claims

In Column 11, Line 22: "first second" should be -- second --.

Signed and Sealed this
Twenty-seventh Day of January, 2026

John A. Squires
*Director of the United States Patent and Trademark Office*